United States Patent [19]
Schoenmeyr et al.

[11] Patent Number: 5,494,573
[45] Date of Patent: Feb. 27, 1996

[54] REVERSE OSMOSIS WATER PURIFICATION DIAGNOSTIC SYSTEM

[75] Inventors: Ivar Schoenmeyr, Mission Viejo; Mike Mihld, Murrieta, both of Calif.

[73] Assignee: Aquatec Water Systems, Inc., Anaheim, Calif.

[21] Appl. No.: 195,879

[22] Filed: Feb. 14, 1994

[51] Int. Cl.⁶ .................................................. B01D 65/10
[52] U.S. Cl. ................. 210/94; 210/257.2; 210/258; 222/23; 222/189.01; 345/25; 417/63
[58] Field of Search ............................ 210/85, 96.1, 96.2, 210/143, 257.2, 94, 95, 258, 259; 222/23, 52, 189; 364/132, 479; 417/63; 345/25

[56] References Cited

U.S. PATENT DOCUMENTS

| | | | |
|---|---|---|---|
| 3,838,774 | 10/1974 | Dolan et al. | 210/85 |
| 3,856,676 | 12/1974 | Grimme | 210/257.2 |
| 3,990,066 | 11/1976 | Malmgren | 340/285 |
| 3,992,301 | 11/1976 | Shippey et al. | 210/90 |
| 4,160,727 | 7/1979 | Harris | 210/257.2 |
| 4,498,982 | 2/1985 | Skinner | 210/96.2 |
| 4,528,093 | 7/1985 | Winer | 210/257.2 |
| 4,587,518 | 5/1986 | King | 340/603 |
| 4,741,823 | 5/1988 | Olsen et al. | 210/96.2 |
| 4,744,895 | 5/1988 | Gales et al. | 210/96.2 |
| 4,773,991 | 9/1988 | Aid | 210/96.2 |
| 4,784,763 | 11/1988 | Hambleton et al. | 210/90 |
| 4,784,771 | 11/1989 | Wathen et al. | 210/636 |
| 4,801,375 | 1/1989 | Padilla | 210/257.2 |
| 4,806,912 | 2/1989 | Clack | 340/603 |
| 4,842,723 | 6/1989 | Parks et al. | 210/95 |
| 4,851,818 | 7/1989 | Brown et al. | 340/603 |
| 5,004,535 | 4/1991 | Bosko et al. | 210/90 |
| 5,061,374 | 10/1991 | Lewis | 210/638 |
| 5,096,574 | 3/1992 | Birdsong et al. | 210/90 |
| 5,174,901 | 12/1992 | Smith | 210/257.2 |
| 5,328,597 | 7/1994 | Boldt et al. | 222/189.06 |
| 5,427,682 | 6/1995 | Vogel et al. | 210/257.2 |
| 5,443,739 | 8/1995 | Vogel et al. | 210/257.2 |

FOREIGN PATENT DOCUMENTS

| | | | |
|---|---|---|---|
| 464321 | 1/1992 | European Pat. Off. | 210/96.2 |
| 3206589 | 9/1991 | Japan | 222/23 |
| 92008671 | 5/1992 | WIPO | 222/23 |

*Primary Examiner*—Joseph W. Drodge
*Attorney, Agent, or Firm*—Blakely, Sokoloff, Taylor & Zafman

[57] ABSTRACT

A monitor for a beverage processing system that can sense a characteristic of the system, compare the characteristic to a threshold value to determine if a component of the system is not operating properly, and transmit the characteristic to a remote site. The monitor includes a controller coupled to a number of sensors that sense various system characteristics such as the water pressure and resistance at various locations of the system. The processor compares the outputs of the sensors with threshold values to determine if the various components are operating properly. The monitor also has a visual display unit which can output the various characteristic values along with processor generated messages that identify a component(s) that is not operating properly or needs preventive maintenance. The monitor transmits data via a modem to a computer located at a remote site. The computer can store and display the characteristics and other processor outputs.

7 Claims, 6 Drawing Sheets

REVERSE OSMOSIS WATER PURIFICATION DIAGNOSTIC SYSTEM

BACKGROUND OF THE INVENTION

1. Field of the Invention

The present invention relates to a monitor system for a beverage processing system such as a reverse osmosis water purification system.

2. Description of Related Art

Reverse osmosis (RO) water purification systems are used to purify water. The purified water can be used for drinking water, fabricating silicon wafers and various other applications. RO systems typically have an osmotic membrane that removes impurities from the water. The RO system may also have a pump to push the water through the membrane and a number of filters to remove sediments and other impurities. The purified water is typically stored in a holding tank or pressurized accumulator for subsequent use.

To test the purity of the processed water, some RO systems utilize sensors and accompanying circuitry to measure the resistance of the water at both the inlet and outlet of the osmotic membrane. U.S. Pat. No. 3,838,774 issued to Dolan et al; U.S. Pat. No. 4,806,912 issued to Clack and U.S. Pat. No. 4,851,818 issued to Brown et al, all disclose devices that monitor the quality of water in a water purification system. The prior art water quality monitors typically compare the resistance values to a threshold value. If the relative resistance values exceed the threshold value, an indicator light is illuminated to indicate that the threshold has been exceeded. Illumination of a red light may indicate to the user that the system is not operating properly.

Although monitor systems of the prior art can provide an indication that the overall system is not operating properly, these monitors can not identify which discrete elements of the system have malfunctioned. The poor water quality may be caused by a clogged osmotic membrane, expired carbon filter or degradation of the sediment filter. Repairing the system may require an inspection of numerous components, thereby increasing the time and possibly the cost of fixing the unit. Additionally, the monitors of the prior art do not provide an indication of when the system is about to fail. It would be desirable to initiate preventative maintenance on an RO unit before a system failure. System failure may result in an extended period of non-use.

It would be desirable to provide a water purification monitor system that can determine the working status of each element of the system and to provide an indication to the user of the status. It would also be desirable to remotely monitor the various characteristics of the purification system, so that system errors can be remotely diagnosed, and preventive maintenance can be initiated without periodic on-site inspection.

SUMMARY OF THE INVENTION

The present invention is a monitor for a beverage processing system that can sense a characteristic of the system, compare the characteristic to a threshold value to determine if a component of the system is not operating properly, and transmit the characteristic to a remote site. The monitor includes a controller coupled to a number of sensors that sense various system characteristics such as the water pressure and resistance at various locations of the system. The processor compares the outputs of the sensors with threshold values to determine if the various components are operating properly. The monitor also has a visual display unit which can output the various characteristic values along with processor generated messages that identify a component(s) that is not operating properly, or needs preventive maintenance.

The monitor transmits data via a modem to a computer located at a remote site. The computer can store and display the characteristics and other processor outputs. The monitor of the present invention thus allows the purification system to be remotely monitored and diagnosed.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
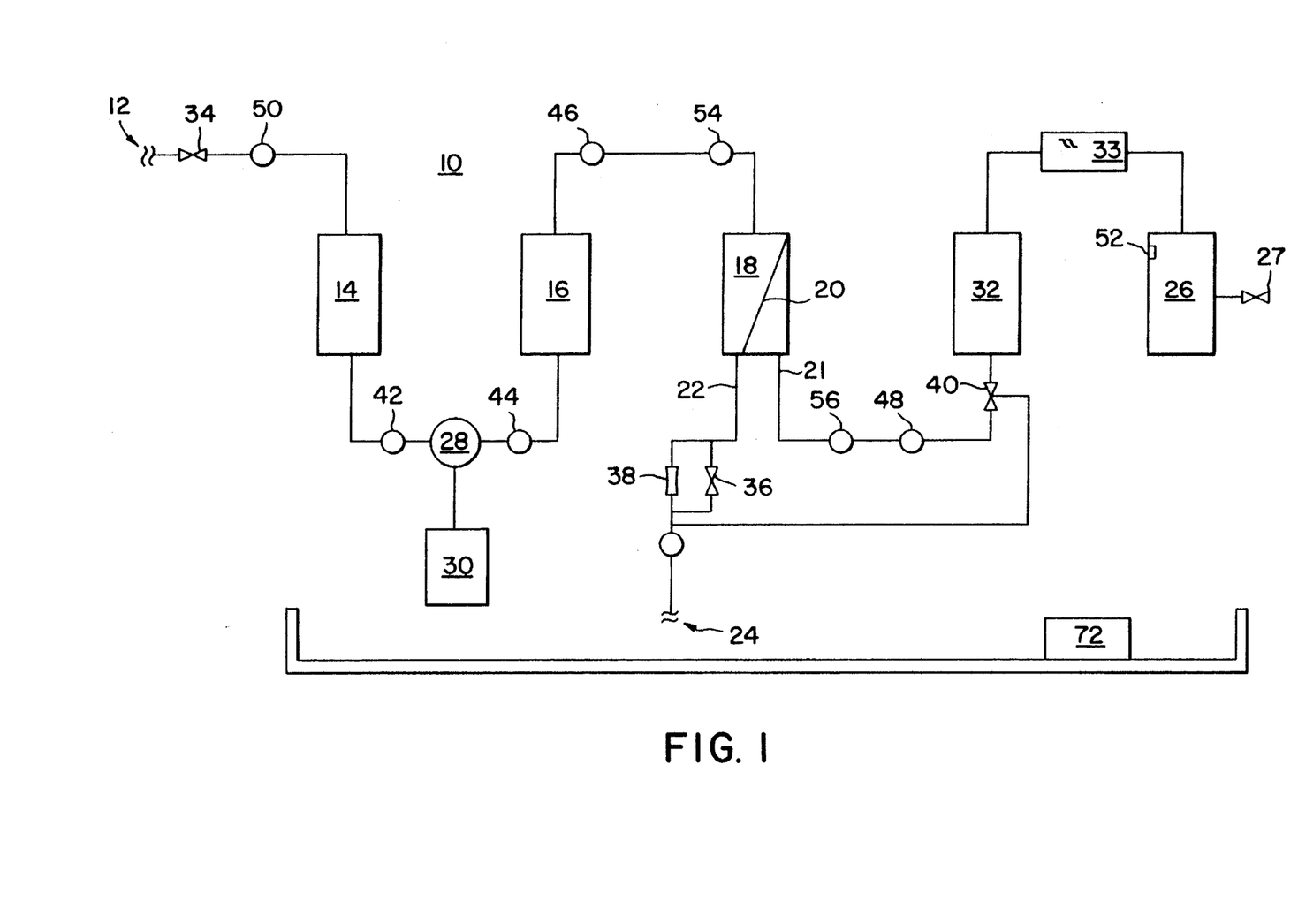
FIG. 1 is a schematic of a reverse osmosis water purification system of the present invention.

Referring to the drawings more particularly by reference numbers, FIG. 1 shows a schematic of a reverse osmosis water purification system 10. The system 10 is typically connected to a source of water 12. The water source 12 is typically a municipal water supply. The system 10 may include a sediment filter 14 that is coupled to the water source 12 and which removes sediments from the water. Coupled to the sediment filter 14 is a pre-carbon filter 16 which absorbs dissolved gases in the water. The system 10 also has an osmotic membrane filter 18 connected to the pre-carbon filter 16. The osmotic membrane filter 18 contains a membrane 20 that separates remaining impurities in the water. The osmotic filter 18 has both a pure water outlet 21 and a brine water outlet 22. The brine outlet 22 is typically coupled to a drain 24. The pure water outlet 21 is typically coupled to a reservoir 26 that stores the pure water. The reservoir 26 can be either a holding tank or a pressurized accumulator. The water can be removed from the reservoir 26 through valve 27.

The system 10 may contain a pump 28 that pushes the water through the osmotic membrane 18. The pump 28 is typically driven by an electric motor 30. Additionally, the system may include a post-carbon filter 32 and an ultraviolet (UV) filter 33 to further purify the water. The water flow into the system is typically controlled by an inlet valve 34 that can open and close in conjunction with the amount of water within reservoir 26. The brine outlet 22 may be coupled to a flush valve 36 that allows the osmotic membrane 18 to be flushed and cleaned. Also coupled to the brine outlet 22 is a flow regulator 38 which insures a sufficient back pressure in the osmotic filter 18. The system may have a diverter valve 40 which diverts the pure water to drain if the water purity does not meet an acceptable value. The valves 34, 36 and 40 are typically controlled by solenoids. Although a pump, a tank and a number of filter elements and valves are shown and described, it is to be understood that the present invention may be utilized with a variety of different system components.

To monitor the operation of the various system components, the system has a number of sensors. In the preferred embodiment, the system has a first pressure sensor ($P_1$) 42 located at the outlet of the sediment filter 14 and the inlet of the pump 28, a second pressure sensor ($P_2$) 44 located at the outlet of the pump 28 and the inlet of the pre-carbon filter 16, a third pressure sensor ($P_3$) 46 located at the outlet of the pre-carbon filter 16 and the inlet of the osmotic membrane filter 18, and a fourth pressure sensor ($P_4$) 48 located at the outlet of the osmotic membrane filter 18. The pressure sensors 42–48 preferably provide an analog signal with an amplitude that is dependent upon the pressure level of the water. The system 10 may also have a pressure switch 50 located at the inlet of the sediment filter 14. The pressure switch 50 provides a signal when the water pressure into the sediment filter 14 reaches a predetermined value. Alternatively, the switch 50 may be a fifth pressure sensor ($P_5$) which generates an analog signal that correlates to the pressure at the inlet of the sediment filter 14. If the reservoir 26 is a holding tank, the tank may have a level sensor 52 which provides an analog signal that corresponds to the level of water within the reservoir 26.

The system may have a first water resistance sensor 54 and a second water resistance sensor 56 located at the inlet and outlet of the osmotic membrane filter 18, respectively. The sensors 54 and 56 provide analog signals that correlate to the resistance of the water.

Figure 2:
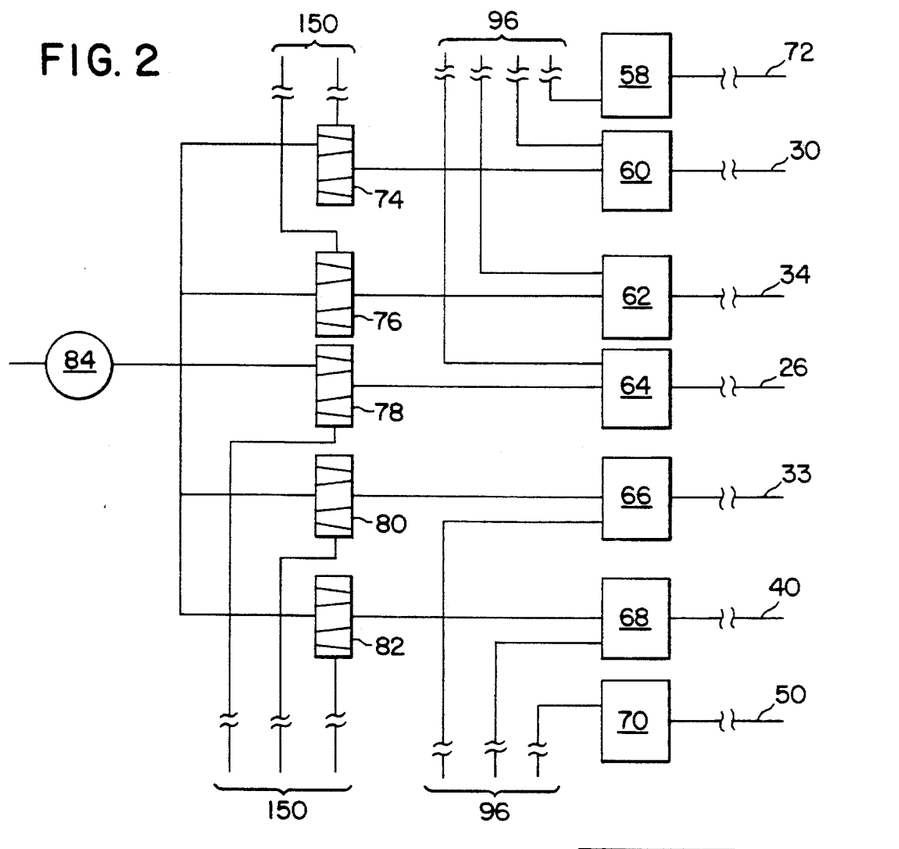
FIG. 2 is a schematic of a input/output circuit of the purification system.

As shown in FIG. 2, the system may also have a number of detection circuits 58–70 that provide an output logic signal when a corresponding element is drawing current. Detection circuit 58 may be coupled to a leak detection sensor 72 located in the trough of the water system. The leak detection sensor 72 detects when water is leaking from the system. The detection circuit 58 provides a digital output signal when the sensor 72 detects a leakage of water.

Detection circuit 60 may be connected to the pump motor 30 to produce an output signal when the motor 30 is "on". Detection circuit 62 may be coupled to the solenoid of the inlet valve 34, such that the circuit 62 provides an output signal when the inlet valve 34 is open. Detection circuit 64 may be coupled to the flush valve 36 to give an indication when the flush valve 36 is open. Likewise, detection circuits 66 and 68 may be connected to the UV filter 33 and diverter valve 40 to determine if these elements are on and open, respectively. Detection circuit 70 may be connected to the pressure switch 50 to provide a digital output signal when the pressure switch is activated.

The detection circuits 60–68 are connected to corresponding triacs 74–82. The triacs 74–82 are connected to a current measuring device 84. The current measuring device provides an analog signal that is proportional to the total current drawn by the system.

Figure 3:
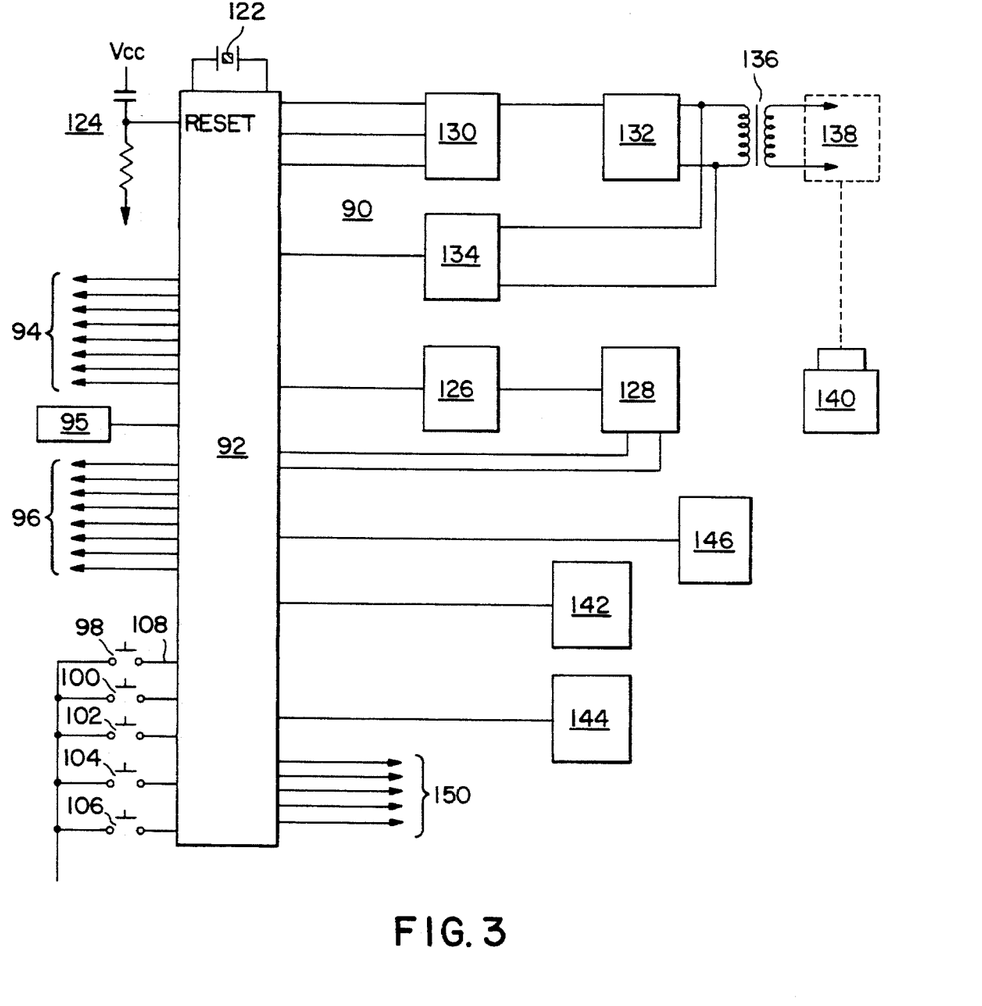
FIG. 3 is a schematic of controller system for the RO unit.

FIG. 3 shows a schematic of a monitor unit 90 that monitors the operation of the water purification system. The monitor unit 90 has a controller 92 with a microprocessor core. In the preferred embodiment, the controller 92 is a microprocessor sold by Signetics Corp. under the designation 80C751. The controller 92 has 8 multiplexed analog inputs 94 that are coupled to an analog to digital (A/D) converter within the controller 92. The analog inputs 94 are connected to the pressure sensors 42–48, level sensor 52 and water resistance sensors 54 and 56. The unit also has a reference voltage circuit 95 that provides a base reference voltage for the A/D converter. The analog signals provided by the sensors and the current meter are converted to digital bit strings by the A/D converter which are then processed by the microprocessor.

The controller 92 also has 8 logic level inputs 96 that are connected to the detection circuits 58–70. The output signals of the detection circuits 58–70 are also processed by the controller 92. The controller 92 also receives logic input signals from switches 98–106 on input lines 108. The switches 98–106 are coupled to the buttons 110–118 located on the front panel 120 of the monitor unit 90 shown in FIG. 4. Depressing a button, closes the corresponding switch and provides an input signal to the controller 92.

The controller 92 is coupled to an oscillator 122 and a reset circuit 124. The oscillator 112 is typically coupled to internal counters within the controller 92 which count in time increments to function as a clock. The oscillator 122 and internal counters are typically used to keep track of the amount of time that the system and/or a particular filter has in been in operation and to measure the time rate of change in the pressure transducers and level sensors. The contents of the internal counters are typically stored in memory so that the controller 92 can output the time value. The reset circuit 124 is connect to a RESET pin of the controller 92. The controller 92 resets when the RESET pin is active.

The controller 92 is connected to a decoder circuit 126 and a liquid crystal display (LCD) module 128. The decoder circuit 126 converts outputs from the controller 92 to alphanumeric characters that are shown by a visual display 129 of the module 126, shown in FIG. 4.

The controller 92 is also coupled to a modem module 130, signal condition circuit 132 and a ring indicator circuit 134. The circuits 132 and 134 are connected to a transformer 136 and a RJ-11 telephone jack 138. The elements 130–138 allow the controller 92 to send data to a remote location. In the preferred embodiment, the controller 92 transmits data to a computer 140. The computer 140 has corresponding hardware and software to communicate with the monitor unit 90.

The controller 92 may also provide outputs to a pair of light emitting diode (LED) indicator circuits 142 and 144. The LED circuits 142 and 144 typically illuminate green and red lights, respectively, to indicate whether the system is operating properly. The controller 92 may also be connected to an alarm 146 circuit which provides an alarm signal (either audio or visual) when the system is not properly operating. The monitor unit 90 is typically coupled to the purification system 10 through an electrical connector 148 that allows the monitor 90 to be readily attached and removed from the system.

Referring to FIG. 3, the controller 92 can also provide output signals on lines 150. The output lines 150 are connected to the gates of the triacs 74–82. The triacs function as switches to the corresponding elements. For example, triac 74 is a switch for the pump 28. The controller 92 can therefore control the operation of the pump 28 through output lines 150 and the triac 74.

The monitor unit 90 monitors the operation of the purification system and provides an indication to the display module 128 and/or computer 140 of the different characteristics of the system. The controller 92 receives input signals from the various input lines, processes the information and then generates an output in accordance with a program stored in a ROM on board the controller 92. In the preferred embodiment the controller 92 provides the following output messages that are displayed on the LCD display and/or computer.

REPLACE SEDIMENT FILTER
REPLACE CARBON FILTER
REPLACE MEMBRANE
CALL FOR SERVICE (PHONE #)
LOW WATER PRESSURE
LEAK DETECTED

The monitor unit of the present invention is thus capable of identifying to the user a specific component that has failed or needs maintenance. The output messages are displayed in accordance with the following algorithms performed by the controller 92.

REPLACE SEDIMENT FILTER output is generated when the differential pressure across the sediment filter exceeds a sediment threshold value (ie. $P_5-P_1>K_1$).

REPLACE MEMBRANE output is generated when the ratio of the water resistance sensors 54 and 56 is less than a osmotic membrane threshold value $K_2$, or the derivative of the fourth sensor pressure $P_4$ over time is less than the differential pressure across the osmotic membrane filter times a membrane constant $K_3$ (ie. $dP_4/dt<K_3\cdot(P_4-P_3)$).

CALL FOR SERVICE is generated when the current measured by the current meter 84 is not within a current threshold bandwidth $K_4$, or differential pressure across the pump is not within a pump threshold bandwidth $K_5$ (ie. $P_2-P_3>K_5$).

LOW WATER PRESSURE is generated when the pressure at the sediment filter inlet ($P_5$) falls below a inlet threshold value $K_6$.

LEAK DETECTED output is generated when the controller receives a logic input from detection circuit 58, which corresponds to a leak detected by leak detection sensor 72.

REPLACE CARBON FILTER output is generated when the operation time of the carbon filter has reached a carbon filter threshold value $K_7$.

Figure 4:
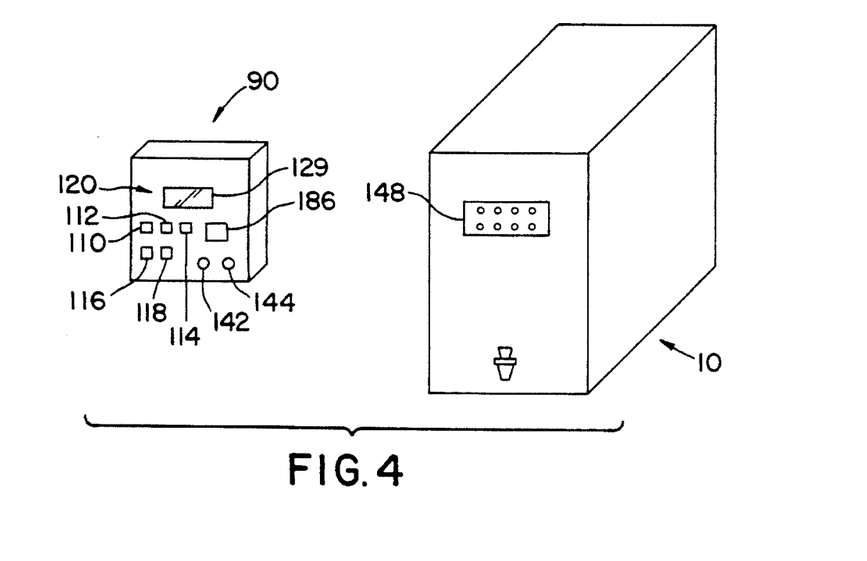
FIG. 4 is a front view of a monitor unit control panel.

The threshold values $K_1$–$K_7$ can be changed by manipulating the buttons 110–118. The buttons 110–118 preferably have the following functions.

110—On/Off; turns the monitor unit on or off.

112—Mode Select; allows the user to select between modes and menus. The modes include an operation mode and a program mode. The operation mode includes the following menus:

TIME/DATE; provides the current time and date.

Hours on Filter: provides the amount of time that a particular filter has been in operation. The selected filter is typically the carbon filter 16.

Rejection Ratio; provides the current resistance ratio measured by the water resistance sensors 54 and 56, thereby giving an indication of the effectiveness of the osmotic membrane 18.

Auto-Timer; is programmable by the user and sets a predetermined time interval at which the purification system will be turned off. The controller counts down the set time and then deactivates the output signal to the triacs 74 and 76 to shut off the inlet valve 34 and the pump 28. The program mode includes the following menus.

Set Ratio xx%: sets the osmotic membrane threshold value $K_2$.

Input Pres. xxpsi: sets the sediment threshold value $K_1$.

Boost Pres. xxpsi: sets the upper and lower limits of the pump threshold bandwidth $K_5$.

Filter Time xx.x min: sets the time interval $K_7$ for the life of the carbon.

Total Current: xx.x: sets the upper and lower limits of the current threshold value $K_4$.

Membrane Constant xx1/sec: sets the membrane constant $K_3$.

Call (Yes)(No): sets whether the controller should call a remote site if the system fails or needs maintenance.

Phone #: sets the phone number that the controller should call.

Reset Alarms (Y)(N): resets the alarm.

Reset Carbon Timer (Y)(N): resets carbon timer.

Self Test (Y)(N); sets whether the monitor unit should perform a self test. The Self Test menu may have submenus to self test memory, CPU etc.

114—Up Select; allows the user to enter the values in the program mode menus and the Auto-timer menu of the operation mode.

116—Down Select; has a function similar to button 114.

118—Enter; allows the user to enter the selected values.

The buttons 110–118 allow the user or an installer to input constants that correlate to the particular filter being installed.

Figure 5A:
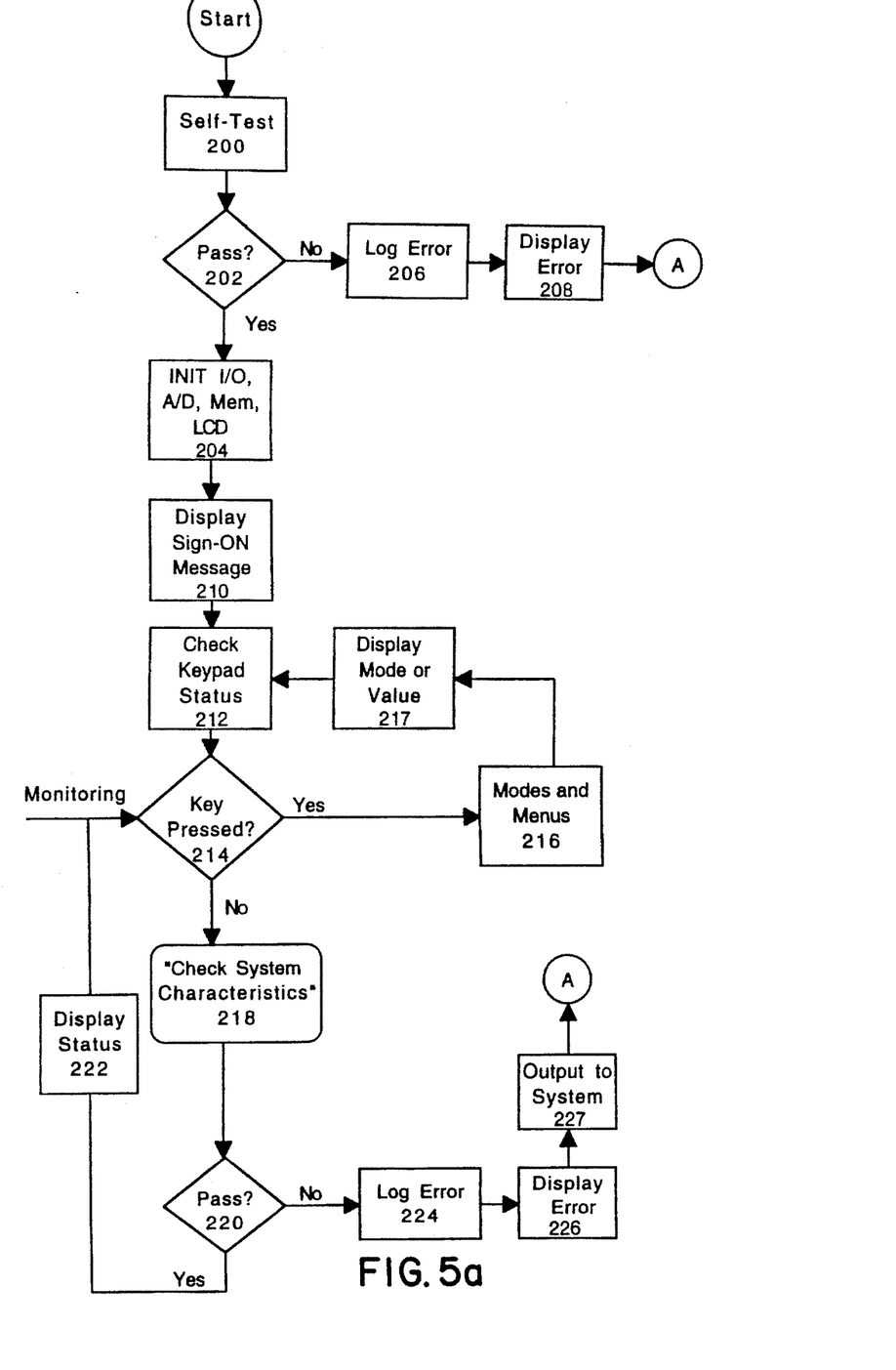
FIGS. 5a–c are flowcharts showing the operation of the monitor unit.
Figure 5B:
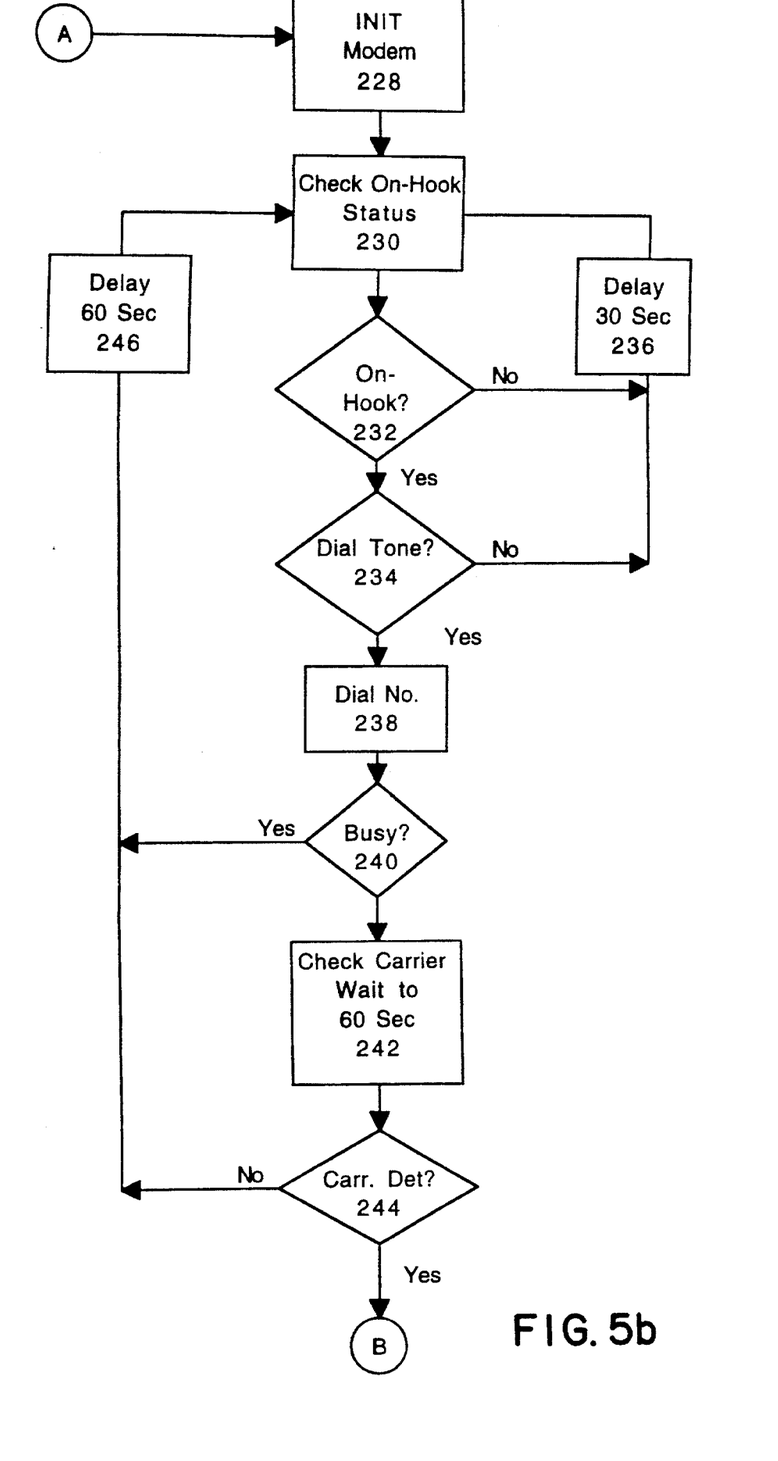
Figure 5C:
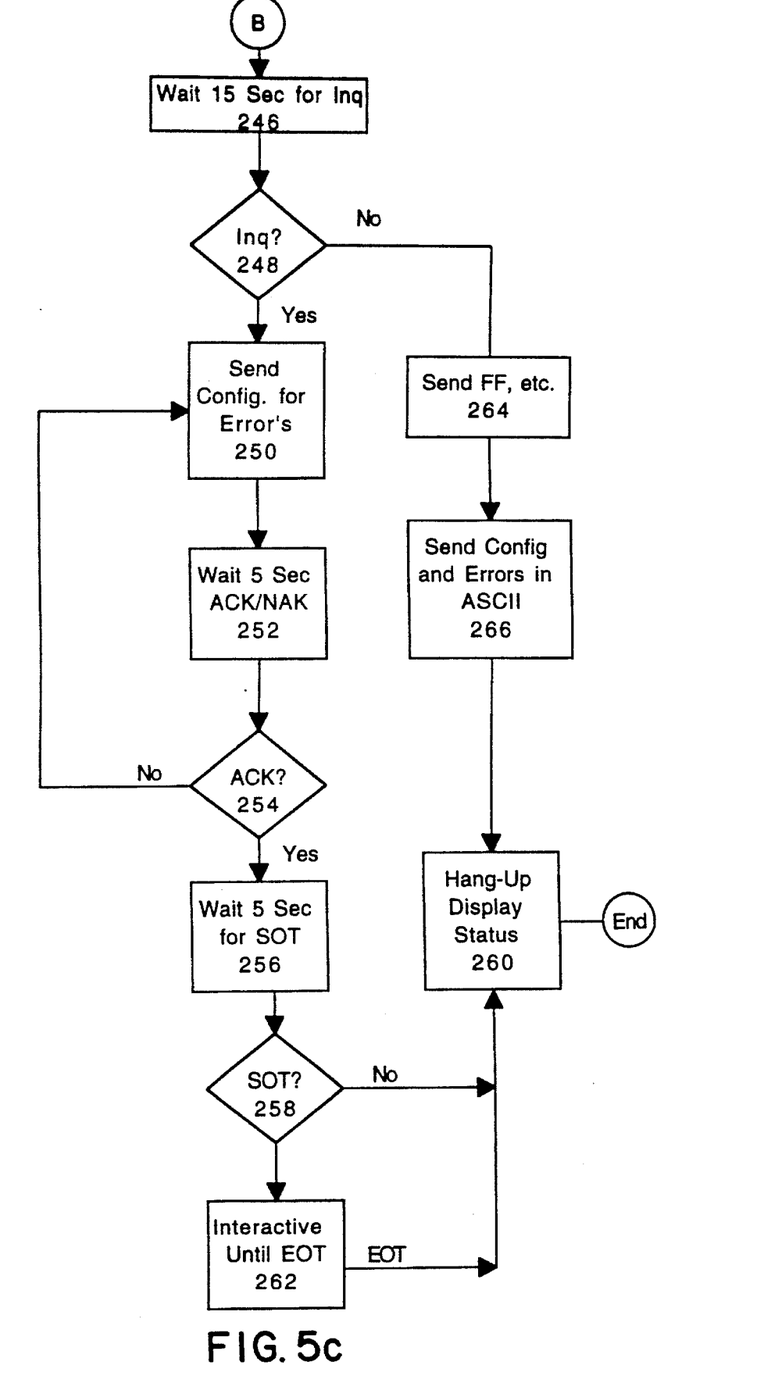

FIGS. 5a–c shows the operation of the monitor unit 92. If the Self Test function has been selected, the controller performs a self test in processing block 200. The process continues to decision block 202. If the unit passes the self test, the controller initializes the various I/O, memory, etc, components of the system in block 204. If the unit fails the self test, the controller logs the error and displays an error message on the display in blocks 206 and 208, respectively. The error message may state for example, MEMORY BAD.

If the system passes self test, the controller then generates a SIGN-ON message on the display 128 in block 210. The process continues to blocks 212 and 214 where the controller 92 determines whether a button 110–118 has been depressed. If a button has been depressed the controller 92 enters the function that corresponds to the button and provides a display in blocks 216 and 217.

If a button has not been depressed, the controller 92 will check the system characteristics through the input lines 94, 96 and 108 in block 218. The controller 92 then processes the input data in decision block 220 to determine if the various characteristics exceed or fall below the threshold values. If the system does not have any components that need service, the process continues to block 222 where the status of the system is displayed by the display. If any error(s) is detected the controller logs and displays the error in blocks 224 and 226, respectively. The error display may include the activation of the red LED circuit and/or the alarm. The controller 92 may also initiate an output signal in block 227. For example, if a leak is detected, the controller may turn off triac 74 and 76 to turn off the pump 28 and inlet valve 34, and generate a message CALL SERVICE. Likewise, if the controller 92 computes that the water resistance ratio of sensors 54 and 56 is below the threshold value $K_2$, then the controller may turn off triac 68 to move the diverter valve 40 so that the permeate water is directed to drain. The controller 92 would also generate the message REPLACE MEMBRANE.

If an error is detected, the process proceeds to block 228 where the controller initializes the modem. The modem will then check to determine if the phone line is on or off hook and whether there is a dial tone, in blocks 230–234. If the phone is off hook, or if there is no dial tone, then the process returns to block 230 after a time delay, which is typically 30 seconds, in block 236.

If the phone is on hook and has a dial tone, the modem will dial the number loaded into the controller and check for a busy signal in blocks 238 and 240. If the dialed line is not busy, the unit will check to determine if there is a compatible carrier on the phone line in blocks 242 and 244. If the line is busy, or the carrier is not compatible, the unit will delay a predetermined time interval in block 246, typically 60 seconds, and then return to processing block 230.

Once the modem is connected, the monitor unit 90 waits a predetermined time interval, typically 15 seconds, for an inquiry from the computer 140 in block 246. If an inquiry is received, then the process continues from decision block 248 to processing block 250, where the unit 90 sends the current error code and configuration to the computer 140. The unit waits for an acknowledgment (ACK) from the computer in blocks 252 and 254. If the unit receives a not acknowledgment (NACK) from the computer 140, then the process returns back to block 250. If the unit receives an ACK signal, the unit waits a predetermined time interval, typically 5 seconds, for a start of text (SOT) response from the computer in blocks 256 and 258. If a SOT is not receive, the unit hangs up and displays the status in block 260. If the unit receives a SOT, then the process proceeds to block 262 where the unit and host interact in accordance with a predetermined protocol until an end of text (EOT) response is received by the unit from the computer. The unit hangs up and provides the status in block 260 when the computer sends an EOT response.

Table I shows a preferred protocol for transmitting data between the unit 90 and the computer 140 in block 262.

TABLE I

| PC | RO | | |
|---|---|---|---|
| ENO | ACK | | |
| ENO | COPYRIGHT | | |
| ACK | *ID | = | 00000000 {cs} {CR,LF} |
| ACK | *PHONE | = | 12345678 {cs} {CR,LF} |
| ACK | *VERSION | = | 1234 {cs} {CR,LF} |
| ACK | *VOLTS | = | 12.34 {cs} {CR,LF} |
| ACK | *AMPS | = | 12.24 {cs} {CR,LF} |
| ACK | *POWER | = | ON {cs} {CR,LF} |
| ACK | *PUMP | = | OFF {cs} {CR,LF} |
| ACK | *RUNNING | = | 123 {cs} {CR,LF} |
| ACK | *HOURS | = | 00000111 {cs} {CR,LF} |
| ACK | *INLET | = | 22.22 {cs} {CR,LF} |
| ACK | *PREFILT | = | 10.33 {cs} {CR,LF} |
| ACK | *PRECARB | = | 12.00 {cs} {CR,LF} |
| ACK | *BACK | = | 15.00 {cs} {CR,LF} |
| ACK | *VALVE1 | = | ON {cs} {CR,LF} |
| ACK | *VALVE2 | = | OFF {cs} {CR,LF} |
| ACK | *VALVE3 | = | ON {cs} {CR,LF} |
| ACK | *PRM | = | BAD {cs} {CR,LF} |
| ACK | *ERROR | = | PRM {cs} {CR,LF} |
| ACK | EOT | | |

The commands are all preceded by an asteriks. The records consist of a label and a data field separated by an ASCII equal sign. The label is typically 8 bytes long and the data field is typically 12 bytes long. Each record is followed by a check sum (cs), a carriage return (CR) and a line feed (LF). A COPYRIGHT notice is initially sent to insure that the unit is running with authorized firmware. The ID and PHONE commands identify the unit to the host computer 140. The VERSION command specifies the version of software being used by the unit. The remaining records provide the following data.

VOLTS; voltage of the unit power supply.

AMPS; current of the unit power supply.

POWER; indication of whether the system is on.

PUMP; indication of whether the pump is on.

RUNNING; batch time of system.

HOURS; accumulated time of system.

INLET; pressure at the inlet of the system.

PREFILT; pressure differential across sediment filter.

PRECARB; time that carbon filter has been in operation.

MEMBRANE; differential membrane output pressure in time ($dP_4/dt$).

VALVE1; indication of whether the inlet valve is on.

VALVE2; indication of whether the flush valve is on.

VALVE3; indication of whether the diverter valve is on.

PRM; ratio of water resistance of osmotic membrane.

ERROR; indication of a type of error. For example, the error message may be REPLACE MEMBRANE.

Referring to FIG. 5c, if the computer does not send an inquiry, the unit will assume an ASCII mode and send the configuration and error data along with the appropriate form feed (FF), CR and LF messages in blocks 264 and 266.

The host computer 140 can receive, store and display the data. The computer is typically a personal computer that can store the various system characteristics in defined fields. The computer can display the unit ID and a corresponding address/phone number to a viewer in the remote location, so that the view can associate the data and error messages with the unit and initiate a maintenance routine for the unit. The computer can also sort and tabulate the data in a variety of different manners.

The present invention thus monitors a beverage processing system such as an RO unit and identifies specific errors in the system. The present invention also allows the RO unit to be monitored off-site so that the system may be repaired or maintained by an outside service.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A reverse osmosis water purification unit, comprising:

a housing which has an inlet port and an outlet port;

a pump that is located within said housing and connected to said inlet port;

a reverse osmosis membrane that is located within said housing and connected to said pump;

a tank that is located within said housing and connected to said reverse osmosis membrane and said outlet port;

a pump monitor that monitors said pump and provides a pump monitor output signal;

a membrane monitor that monitors said reverse osmosis membrane and provides a membrane monitor output signal;

a controller attached to said housing, said controller receiving said pump monitor output signal and said membrane output signal to determine a pump fault condition of said pump and a membrane fault condition of said reverse osmosis membrane, said controller operable to generate a pump output signal when there is the display fault condition and operable to generate a membrane display output signal when there is the membrane fault condition;

an alphanumeric display that is mounted to said housing and connected to said controller and which is operable to display a pump alphanumeric message in response to said pump display output signal and is operable to display a membrane alphanumeric message in response to said membrane display output signal.

2. The unit as recited in claim 1, further comprising a carbon filter that is connected to said pump and a carbon filter monitor that monitors said carbon filter and provides a carbon filter output signal that is received by said controller to determine a carbon filter fault condition, said controller generates a carbon filter display output signal when there is the carbon filter fault condition, and said alphanumeric display displays a carbon filter alphanumeric message in response to said carbon filter display output signal.

3. The unit as recited in claim 1, further comprising a sediment filter that is connected to said pump and a sediment filter monitor that monitors said sediment filter and provides a sediment filter output signal that is received by said controller to determine a sediment filter fault condition, said controller generates a sediment filter display output signal when there is the sediment filter fault condition, and said alphanumeric display displays a sediment filter alphanumeric message in response to said sediment filter display output signal.

4. The unit as recited in claim 1, further comprising a sensor that detects a leakage of water in said housing and a water leakage monitor that monitors said water leakage and provides a water leakage output signal that is received by said controller to determine a water leakage fault condition, said controller generates a water leakage display output signal when there is the water leakage fault condition, and said alphanumeric display displays a water leakage alphanumeric message in response to said water leakage display output signal.

5. The unit as recited in claim 1, wherein said controller is located within an external module that is mounted to said housing by an electrical connector located on an outer surface of said housing.

6. The unit as recited in claim 1, further comprising an alarm that is energized by said controller when a fault condition exists.

7. The unit as recited in claim 1, further comprising a communication link coupled to said controller to provide data associated with the fault conditions to a remote location.

* * * * *